United States Patent
Danks et al.

[11] Patent Number: 5,989,228
[45] Date of Patent: Nov. 23, 1999

[54] TROCAR FLAPPER VALVE

[75] Inventors: John K. Danks, Delray Beach, Fla.; Thomas R. Johnson, Milford, N.H.

[73] Assignee: Endoscopic Concepts, Inc.

[21] Appl. No.: 08/695,476

[22] Filed: Aug. 13, 1996

Related U.S. Application Data

[63] Continuation of application No. 08/238,959, May 6, 1994, Pat. No. 5,545,150.

[51] Int. Cl.⁶ ..................................................... A61M 5/00
[52] U.S. Cl. ..................... 604/256; 604/167; 251/149.1
[58] Field of Search ..................... 604/164, 167, 604/169, 246, 256, 264; 251/149.1, 149.2

[56] References Cited

U.S. PATENT DOCUMENTS

| | | | |
|---|---|---|---|
| 4,654,030 | 3/1987 | Moll et al. | 604/165 |
| 4,673,393 | 6/1987 | Suzuki et al. | 604/167 |
| 4,902,280 | 2/1990 | Lander | 604/165 |
| 4,943,280 | 7/1990 | Lander | 604/169 |
| 5,009,391 | 4/1991 | Steigerwald | 604/167 |
| 5,030,206 | 7/1991 | Lander | 604/164 |
| 5,041,095 | 8/1991 | Littrell | 604/167 |
| 5,053,016 | 10/1991 | Lander | 604/169 |
| 5,104,383 | 4/1992 | Shichman | 604/167 |
| 5,122,122 | 6/1992 | Allgood | 604/174 |
| 5,127,909 | 7/1992 | Shichman | 604/165 |
| 5,129,885 | 7/1992 | Green | 604/164 |
| 5,226,891 | 7/1993 | Bushatz et al. | 604/165 |
| 5,256,149 | 10/1993 | Banik et al. | 604/164 |
| 5,273,545 | 12/1993 | Hunt et al. | 604/167 |
| 5,314,417 | 5/1994 | Stephens et al. | 604/264 |
| 5,364,372 | 11/1994 | Danks et al. | 604/264 |
| 5,385,552 | 1/1995 | Haber | 604/169 |
| 5,385,553 | 1/1995 | Hart et al. | 604/167 |
| 5,445,617 | 8/1995 | Yoon | 604/165 |

*Primary Examiner*—Corrine McDermott
*Attorney, Agent, or Firm*—Miller & Miller, LLP

[57] ABSTRACT

A trocar is formed from a cannula and an interfitting obturator for penetrating body cavity walls in laparoscopic and endoscopic surgery. The cannula has an improved inexpensive flexible flapper valve and can be manufactured with a reusable cannula tube but disposable flapper valve assembly to minimize cost.

13 Claims, 2 Drawing Sheets

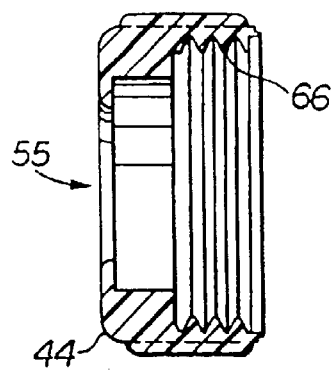
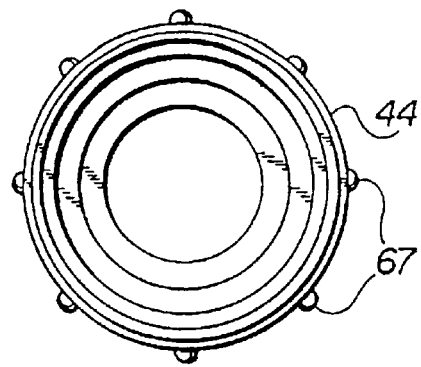
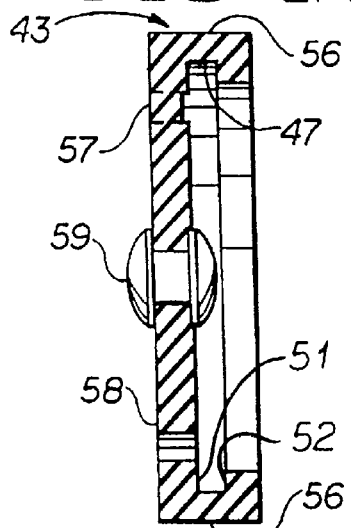
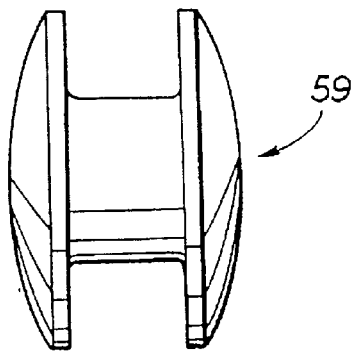
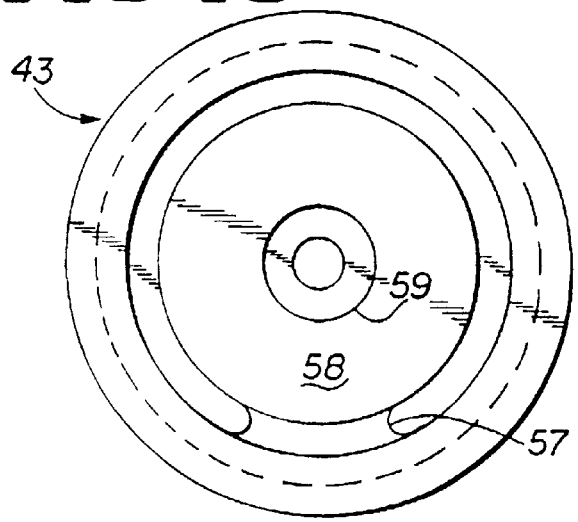
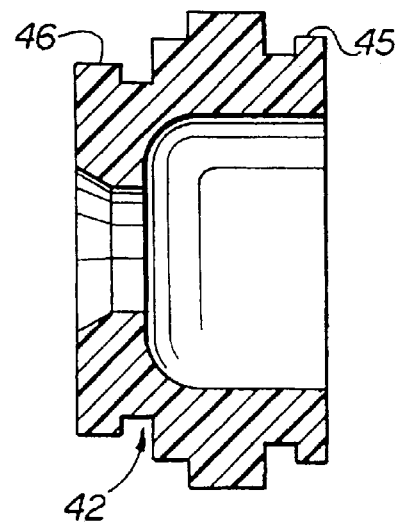

TROCAR FLAPPER VALVE

This is a continuation of U.S. application Ser. No. 08/238,959 filed May 6, 1994 which issued as U.S. Pat. No. 5,545,150 on Aug. 13, 1996.

BACKGROUND OF THE INVENTION

The present invention relates to a surgical instrument commonly referred to as a trocar, or an obturator and cannula, often used in laparoscopic or arthroscopic surgery. More particularly, the invention relates to a new and improved design for a flapper valve, seal, and to the use of disposable seal assemblies on an otherwise reusable instrument.

Many surgical procedures are now being performed with the use of trocars and cannulas. Originally these devices were used for making a puncture and leaving a tube to drain fluids. As technology and surgical techniques have advanced, it is now possible to insert surgical instruments through the cannulas and perform invasive procedures through openings less than half an inch in diameter. Previously these procedures required incisions of many inches. By minimizing the incision, the stress and loss of blood suffered by patients is reduced and the patients' recovery times are dramatically reduced.

Surgical trocars are most commonly used in laparoscopic surgery. Prior to use of the trocar, the surgeon will usually introduce a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, pneumoperitoneum is created separating the wall of the body cavity from the internal organs.

A trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or camera may be inserted through the cannula to view the body cavity, or surgical instruments may be inserted to perform ligations or other procedures.

Once the cannula has been introduced into the opening in the body cavity wall, the pneumoperitoneum may be maintained by introducing gas into the abdominal cavity through the cannula. Various seals and valves have been utilized to allow abdominal pressure to be maintained in this fashion. Maintaining abdominal pressure is important both to allow working room in the body cavity for instruments introduced through the cannula, and to provide free space for the puncturing of the body cavity wall by one or more additional trocars as may be required for some procedures.

While the existing trocars and cannulas have proven useful, several disadvantages remain.

Also, with the current emphasis on cost controls in health care, it is desirable to utilize reusable medical instruments whenever possible. The difficulties of cleansing, disinfecting and otherwise decontaminating used trocars has made this a time consuming or impossible task, especially for the mechanisms contained in shielded trocars. Therefore, a need exists for an improved apparatus for performing laparoscopic and similar surgical procedures.

SUMMARY OF THE INVENTION

Accordingly, it is an object of the invention to provide a cannula which may be substantially reused without the need for excessive labor in cleaning and decontamination.

It is another object of the invention to provide a seal or valve which permits easy insertion of surgical and exploratory instruments through the cannula yet still operates effectively to maintain the pneumoperitoneum in the body cavity.

It is yet another object of the invention to provide an inexpensive and easily assembled seal or valve assembly.

Accordingly, the present invention provides a cannula with a detachable cap and disposable seal assembly. A novel and inexpensive flexible valve is also provided which facilitates insertion of surgical instruments.

BRIEF DESCRIPTIONS OF THE DRAWINGS

FIG. 3A is a cross sectional side view of the end cap of the improved cannula of FIG. 1 in isolation.

FIG. 3B is an end view of the end cap of the improved cannula of FIG. 1.

FIG. 4A is a cross sectional side view of the flexible flapper valve of the improved cannula of FIG. 1 in isolation.

FIG. 4B is an enlarged side plan view of the button which is mounted in the center of the preferred embodiment of the flexible flapper valve.

FIG. 4C is an end view of the flexible flapper valve of the improved cannula of FIG. 1.

FIG. 5 is a cross sectional side view of the gland retainer of the improved cannula of FIG. 1 shown in isolation.

DESCRIPTION OF THE PREFERRED EMBODIMENTS

Figure 1A:
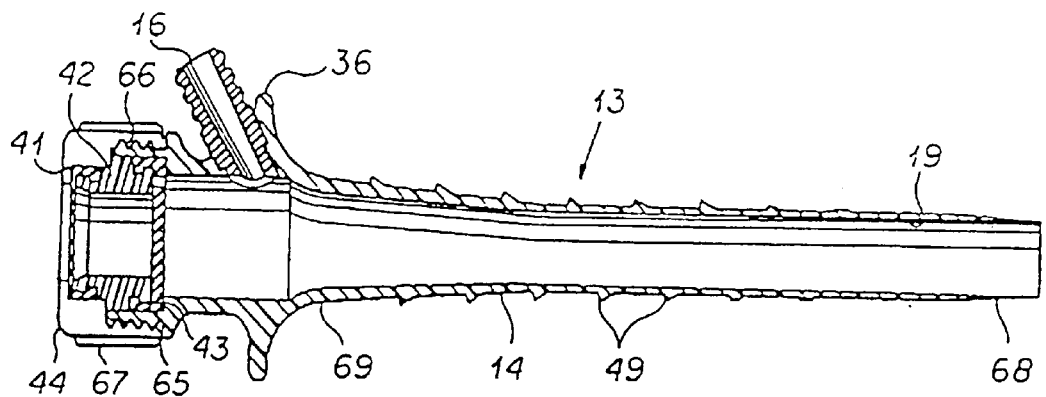
FIG. 1A is a cross sectional side view of an improved cannula according to the invention with a disposable gland retainer and end cap.
Figure 1B:
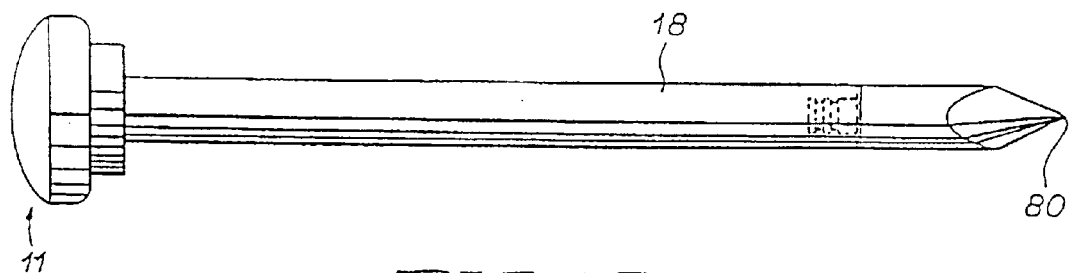
FIG. 1B is a side view of a conventional obturator which is adapted for use with the cannula of FIG. 1A.

The invention commonly known as a trocar is comprised of two major components. These are a cannula 13 such as those illustrated in FIG. 1A, and an obturator such as the traditional obturator 11 with handle 35 in FIG. 1B. The obturator 11 of FIG. 1B and cannula 13 of FIG. 1A are interfitting and as explained below are used together to penetrate a body cavity wall. Once the body cavity wall is penetrated, however, the obturator 11 may be removed and other medical instruments may be introduced into a lumen 19 of the cannula 13.

The cannula 13 of FIG. 1A consists of three components and two seal assemblies. The components are the cannula tube 14, the gland retainer 42 and the cap 44. The outer surface of the cannula tube 14 of FIG. 1A is shown with a helically wound thread 49 preferably beginning at a reduced height a short distance from the distal end 68 of the cannula tube 14 and gradually increasing to its full height as it proceeds toward the proximate end 69. At the proximate end 69 of the cannula tube 14, there is a raised flange 36 for convenience in handling the cannula 13. Above the flange 36 is a gas port 16 which can be connected to a gas supply, not shown, to supply gas through the lumen 19 of the cannula tube 14 into a body cavity to create or maintain pneumoperitoneum. Above the gas port 16 are male threads 65 which allow the cannula tube 14 to be securely coupled with cap 44 which has corresponding female threads 66. The cap 44 also has an aperture 55 to permit insertion of an obturator 11, and gripping protrusions 67 to facilitate fastening and unfastening the cap 44. Mounted concentrically mostly within the proximate end 69 of the cannula tube 14 and held in place by the cap 44 is the gland retainer 42. The cap 44 is shown in isolation in FIGS. 3A and 3B. It will be noted that at the proximate end 69 of cannula tube 14, the lumen 19 is of larger diameter than at the distal end 68, and forms a proximate cavity 37 that both receives the gland retainer 42 and extends somewhat further toward the distal end 68.

Figure 2:
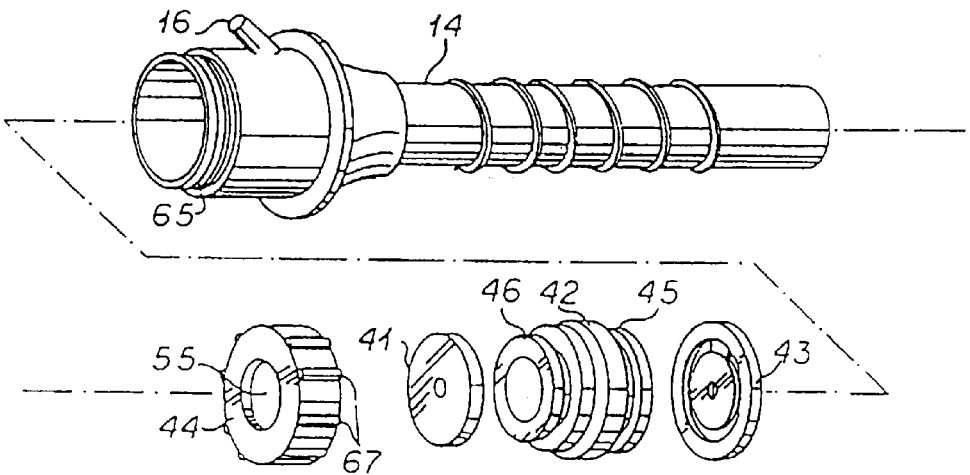
FIG. 2 is an exploded perspective view of the improved cannula of FIG. 1.

The gland retainer 42 shown in isolation in FIG. 5, holds two seals, 43 and 41, in place. Flexible flapper seal 43 shown in FIG. 4A has a fastening section such as the illustrated annular outer casing 56 which engages the gland retainer. A raised edge 45 at the distal end of the gland retainer 42 fits within a channel 47 shown in FIG. 4A formed by the lips 51, 52 of the C shaped edge comprising the outer casing 56 of flexible flapper seal 43, shown in FIGS. 1A and 2. A corresponding groove 48 located toward the distal end of the gland retainer 42 receives the first lip 51 of the flexible flapper seal 43. A second raised edge 46 at the proximate end of the gland retainer 42 fits with a channel formed by a similar C shaped edge of the outer casing wiper seal 41 opposite that shown in FIG. 4A. Both the membrane seal 41 and flexible flapper seal 43 are fabricated from materials having sufficient elasticity that the edges of the seals 41 and 43 can be stretched over ridges 46 and 45 respectively.

The wiper seal 41 is of conventional design, however, the flexible flapper valve 43 is of novel construction. As shown in FIGS. 4A and 4C, a hinge 57 extends inward from the outer casing 56 of the flexible flapper valve 43 and mounted on the hinge is the generally circular flapper portion 58. The flapper portion 58 of flapper valves 43 according to present invention are of greater width than the hinge 57. To prevent the flapper portion 58 from binding with the outer casing 56, an annular slot 50 separates those elements except at hinge 57. The flapper 58 is preferably molded or stamped in one piece with the hinge 57 and outer casing 56 of an elastomeric material. In the preferred embodiment a hard plastic or metal button 59 is mounted on or through the flapper. Preferably the button 59 has an upper surface 63, a post 62 penetrating the flapper portion 58, and a bottom surface 61. When the piercing tip 80, shown in FIG. 1A, of an obturator 11 is inserted through the opening 55 in the cap 44, and through the wiper seal 41, the piercing tip contacts the hard button 59 of the flexible flapper valve 43 and begins to deflect the flapper 58 from its normal closed position flush against the distal end surface 30 of the gland retainer 42. In the absence of button 59, the piercing tip of the obturator might otherwise penetrate or cut into the flapper 58 which could cause resistance to entry of the obturator or damage the flapper 58 so that it would no longer seal the cannula 13 or gland retainer 42 effectively against loss of air through the opening 55 in the cap 44. The hard button 59 alleviates these possible problems and also adds rigidity to the flapper 58. The end surface 30 of the gland retainer is substantially planar defining a shelf within the cannula tube lumen around an opening or flapper valve aperture 31 at least as large as the cannula lumen 19, but smaller than flapper 58. When assembled in the proximate end 69 of the cannula 13, the end surface 30 forms a shelf around opening 31.

Proceeding toward the end cap 44 at the proximal end of the cannula, the opening 31 in the illustrated gland retainer 42 tapers to a fitted aperture 32 of substantially equal diameter to the cannula lumen 19. The proximal opening 33 of the gland retainer 42 is preferably slightly larger than the cannula lumen 19 so that the obturator 11 or other instrument being inserted will be guided through the fitted aperture 32 and on through the gland retainer 42 into contact with button 59 on the flapper 58.

When the obturator 11 or other endoscopic instrument is removed from the cannula 13, the resiliency of the hinge 57 causes the flapper 58 to move to a partially closed position. The flapper 58 is then firmly closed and sealed against the distal end surface 30 of gland retainer 42 by action of the air pressure from the inflated body cavity. The air pressure pushing the flapper 58 against the distal end surface 30 of the gland retainer 42 thereby closes opening 31 and forms an effective seal against further loss of gas.

In its preferred embodiment, the cannula tube 14 portion is manufactured of a durable material such as stainless steel or titanium alloys, capable of withstanding repeated high temperature cleaning and sterilization, while the gland retainer 42 is made of an inexpensive plastic. The cap 44 may be made of either type of material. The gland retainer 42, containing the flapper valve 43 and possibly also containing a wiper seal 41, is difficult to clean and sterilize. However, the gland retainer 42 and seals 41 and 43 are relatively inexpensive to manufacture and can be discarded after each use. The cannula tube 14, and optionally the cap 44, are relatively easy to clean and sterilize and need not be discarded. By reusing the cannula tube 14, and the cap 44 if manufactured of an appropriate material, cost and waste can be minimized. If desired the cap 44 can also be manufactured of inexpensive plastic and discarded with the gland retainer 42 after use.

Numerous alterations of the structures herein described will suggest themselves to those skilled in the art. It will be understood that the details and arrangements of the parts that have been described and illustrated in order to explain the nature of the invention are not to be construed as any limitation of the invention. All such alterations which do not depart from the spirit of the invention are intended to be included within the scope of the appended claims.

We claim:

1. A cannula comprising:
    (a) a cannula tube with an outer surface and an interior lumen, and having a forward distal end and a rearward proximate end, wherein said lumen has an enlarged cavity portion intermediate said distal end and said proximate end;
    (b) a shelf extending inwardly from the cannula tube in the enlarged cavity portion defining a flapper valve aperture;
    (c) a flapper valve, mounted adjacent to and forward of said shelf, having an integral hinge and a flapper formed of elastomeric material, and wherein the size of said flapper is larger than the flapper valve aperture; and
    (d) a hard button located on the flapper wherein the size of the hard button is smaller than the flapper valve aperture.

2. The cannula of claim 1 wherein the hinge permits the flapper to fold forward into the enlarged cavity portion toward the distal end of the cannula and wherein the inwardly extending shelf restricts the flapper from folding rearward toward the proximate end of the cannula.

3. The cannula of claim 2 wherein air pressure from the distal end of the cannula tube forces the flapper rearward against the inward extending shelf thereby substantially sealing the distal end of the cannula tube.

4. The cannula of claim 1 wherein the flapper has a width relatively greater than the width of the hinge.

5. The cannula of claim 1 wherein the button is mounted on the flapper, said button being relatively harder than the flapper portion.

6. A cannula comprising:
(a) a cannula tube with an outer surface and an interior lumen, and having a forward distal end and a rearward proximate end, wherein said lumen has an enlarged cavity portion intermediate said distal end and said proximate end;
(b) a shelf extending inwardly from the cannula tube in the enlarged cavity portion defining a flapper valve aperture, said inwardly extending shelf is defined by a gland retainer; and
(c) a flapper valve, mounted adjacent to and forward of said shelf, having an integral hinge and a flapper formed of elastomeric material and wherein the size of said flapper is larger than the flapper valve aperture, said hinge permits the flapper to fold forward into the enlarged cavity portion toward the distal end of the cannula and wherein the inwardly extending shelf restricts the flapper from folding rearwardly toward the proximate end of the cannula.

7. A cannula comprising:
(a) a cannula tube with an outer surface and an interior lumen, and having a forward distal end and a rearward proximate end, wherein said lumen has an enlarged cavity portion intermediate said distal end and said proximate end;
(b) a shelf extending inwardly from the cannula tube in the enlarged cavity portion defining a flapper valve aperture;
(c) a flapper valve, mounted forward of said shelf, having an integral hinge and a flapper formed of elastomeric material, and wherein the size of said flapper is larger than the flapper valve aperture and the flapper valve has a fastening section which is formed of a unitary piece of elastomeric material with the hinge and flapper; and
(d) a hard button located on the flapper, wherein the size of the hard button is smaller than the flapper valve aperture.

8. A cannula comprising:
(a) a cannula tube with an outer surface and an interior lumen, and having a forward distal end and a rearward proximate end, wherein said lumen has an enlarged cavity portion intermediate said distal end and said proximate end;
(b) a shelf extending inwardly from the cannula tube in the enlarged cavity portion defining a flapper valve aperture; and
(c) a flapper valve, mounted forward of said shelf, having an integral hinge and a flapper formed of elastomeric material, and wherein the size of said flapper is larger than the flapper valve aperture and the flapper valve has a fastening section which is formed of a unitary piece of elastomeric material with the hinge and flapper, and said fastening section having an outer section with a forward lip and a rearward lip defining a channel.

9. A cannula comprising:
(a) a cannula tube with an outer surface and an interior lumen, and having a forward distal end and a rearward proximate end, wherein said lumen has an enlarged cavity portion intermediate said distal end and said proximate end;
(b) a gland retainer defining a shelf, said shelf extending inwardly from the cannula tube in the enlarged cavity portion defining, a flapper valve aperture; and
(c) a flapper valve, mounted forward of said shelf, having an integral hinge and a flapper formed of elastomeric material, and wherein the size of said flapper is larger than the flapper valve aperture and the flapper valve has a fastening section comprising an outer section with a channel, said fastening section formed of a unitary piece of elastomeric material with the hinge and flapper.

10. The cannula of claim 9 wherein the gland retainer further comprises a raised edge which is received within the channel of the outer section of the fastening section of the flapper valve.

11. A cannula comprising:
(a) a cannula tube with an outer surface and an interior lumen, and having a forward distal end and a rearward proximate end, wherein said lumen has an enlarged cavity portion intermediate said distal end and said proximate end;
(b) a gland retainer received within the interior lumen of said cannula tube rearward of the enlarged cavity portion and having a distal end surface defining a shelf, said distal end surface also having an opening defining a flapper valve aperture, and said gland retainer also having a raised edge;
(c) a flapper valve having an outer fastening section which defines a channel, said channel being received on the raised edge of the gland retainer, and also having a hinge section connecting said fastening section to a flapper with a relatively hard button being mounted on said flapper and said fastening section, hinge, and flapper all being fabricated from a unitary piece of elastomeric material.

12. A flapper valve comprising a fastening section connected by a hinge to a flapper portion wherein the hinge and flapper portion are formed from a unitary piece of elastomeric material and the flapper is of greater width than the hinge, said fastening section comprising an outer casing having a forward lip and a rearward lip defining a channel.

13. The flapper valve according to claim 12 wherein the fastening section is formed of the same unitary piece of elastomeric material comprising the hinge and flapper portion.

* * * * *